US00PP19347P2

(12) United States Plant Patent
Roberson

(10) Patent No.: US PP19,347 P2
(45) Date of Patent: Oct. 21, 2008

(54) ***LANTANA* PLANT NAMED 'ROBPWCRM'**

(50) Latin Name: *Lantana camara*
Varietal Denomination: Robpwcrm

(76) Inventor: Robert J. Roberson, 31706 E. Pink Hill Rd., Grain Valley, MO (US) 64029

( * ) Notice: Subject to any disclaimer, the term of this patent is extended or adjusted under 35 U.S.C. 154(b) by 0 days.

(21) Appl. No.: 11/978,116

(22) Filed: Oct. 25, 2007

(51) Int. Cl.
*A01H 5/00* (2006.01)

(52) U.S. Cl. ..... Plt./227

(58) Field of Classification Search ..... Plt./227
See application file for complete search history.

*Primary Examiner*—Annette H Para
(74) *Attorney, Agent, or Firm*—C. A. Whealy

(57) ABSTRACT

A new and distinct cultivar of *Lantana* plant named 'Robpwcrm', characterized by its mounding and outwardly spreading plant habit; vigorous growth habit; relatively small leaves; freely flowering habit; and yellow-colored flowers that are held above and beyond the foliage.

1 Drawing Sheet

Botanical designation: *Lantana camara.*
Cultivar denomination: 'Robpwcrm'.

BACKGROUND OF THE INVENTION

The present invention relates to a new and distinct cultivar of *Lantana,* botanically known as *Lantana camara,* and hereinafter referred to by the name 'Robpwcrm'.

The new *Lantana* is a product of a planned breeding program conducted by the Inventor in Grain Valley, Mo. The objective of the breeding program is to create new freely-flowering and vigorous *Lantana* cultivars with outwardly spreading habit and attractive flower coloration.

The new *Lantana* originated from a cross-pollination made by the Inventor in August, 1996 in Grain Valley, Miss. of the *Lantana camara* cultivar Robpatsun, disclosed in U.S. Plant Pat. No. 10,885, as the female, or seed, parent with the *Lantana camara* cultivar Robpatdov, disclosed in U.S. Plant Pat. No. 10,880, as the male, or pollen, parent. The new *Lantana* was discovered and selected by the Inventor as a single flowering plant within the progeny of the stated cross-pollination in a controlled environment in Grain Valley, Mo. in May, 1997.

Asexual reproduction of the new *Lantana* by vegetative cuttings in a controlled environment in Grain Valley, Mo. since October, 1998, has shown that the unique features of this new *Lantana* are stable and reproduced true to type in successive generations.

SUMMARY OF THE INVENTION

The cultivar Robpwcrm has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Robpwcrm'. These characteristics in combination distinguish 'Robpwcrm' as a new and distinct cultivar of *Lantana:*

1. Mounding and outwardly spreading plant habit.
2. Vigorous growth habit.
3. Relatively small leaves.

4. Freely flowering habit.
5. Yellow-colored flowers that are held above and beyond the foliage.

Plants of the new *Lantana* can be compared to plants of the female parent, the cultivar Robpatsun. Plants of the new *Lantana* differ primarily from plants of the cultivar Robpatsun in flower color as plants of the cultivar Robpatsun have darker yellow-colored flowers.

Plants of the new *Lantana* can be compared to plants of the male parent, the cultivar Robpatdov. Plants of the new *Lantana* differ primarily from plants of the cultivar Robpatdov in flower color as plants of the cultivar Robpatdov have creamy white-colored flowers. In addition, plants of the new *Lantana* have darker green-colored leaves than plants of the cultivar Robpatdov.

Plants of the new *Lantana* can be compared to plants of the *Lantana* cultivar New Gold, not patented. Plants of the new *Lantana* differ from plants of the cultivar New Gold in the following characteristics:

1. Plants of the new *Lantana* have larger inflorescences than plants of the cultivar New Gold.
2. Plants of the new *Lantana* have lighter yellow-colored flowers than plants of the cultivar New Gold.

BRIEF DESCRIPTION OF THE PHOTOGRAPHS

The accompanying colored photographs illustrate the overall appearance of the new *Lantana,* showing the colors as true as it is reasonably possible to obtain in colored reproductions of this type. Colors in the photographs may differ slightly from the color values cited in the detailed botanical description which accurately describe the colors of the new *Lantana.*

The photograph at the bottom of the sheet comprises a side perspective view of a typical flowering plant of 'Robpwcrm' grown in a container.

The photograph at the top of the sheet is a close-up view of typical inflorescences and leaves of 'Robpwcrm'.

DETAILED BOTANICAL DESCRIPTION

The aforementioned photographs and following observations and measurements describe plants grown in Bonsall, Calif., under commercial practice during the spring and summer in an outdoor nursery with day temperatures ranging from 13° C. to 38° C. and night temperatures ranging from 10° C. to 24° C. Plants used in the photographs and for the description were grown in one-gallon containers for about four months. In the following description, color references are made to The Royal Horticultural Society Colour Chart, 1995 Edition, except where general terms of ordinary dictionary significance are used.

Botanical classification: *Lantana camara* cultivar Robpwcrm.

Parentage:

*Female, or seed, parent.*—*Lantana camara* cultivar Robpatsun, disclosed in U.S. Plant Pat. No. 10,885.

*Male, or pollen, parent.*—*Lantana camara* cultivar Robpatdov, disclosed in U.S. Plant Pat. No. 10,880.

Propagation:

*Type.*—By vegetative cuttings.

*Time to initiate roots, summer.*—About 12 to 14 days at 26° C.

*Time to initiate roots, winter.*—About 15 to 17 days at 20° C.

*Time to produce a rooted young plant, summer.*—About four weeks at 26° C.

*Time to produce a rooted young plant, winter.*—About five weeks at 20° C.

*Root description.*—Fibrous; medium in thickness; white in color.

*Rooting habit.*—Freely branching; dense.

Plant description:

*Plant habit.*—Initially upright, then outwardly spreading and mounding. Freely branching habit; about six primary lateral branches per plant each with numerous secondary branches; pinching enhances lateral branch development; dense and bushy plant habit. Vigorous growth habit.

*Plant height.*—About 22 cm.

*Plant diameter.*—About 46 cm by 60 cm.

Lateral branch description:

*Length.*—About 28 cm.

*Diameter.*—About 5 mm.

*Internode length.*—About 1.5 cm to 2 cm.

*Strength.*—Strong.

*Texture, young.*—Pubescent; coarse.

*Texture, mature.*—Woody.

*color, young.*—146C.

*Color, mature.*—199A to 199B.

Foliage description:

*Arrangement.*—Opposite, simple.

*Length.*—About 4.5 cm.

*Width.*—About 2.2 cm.

*Shape.*—Ovate to lanceolate.

*Apex.*—Acute.

*Base.*—Obtuse to attenuate.

*Margin.*—Serrate.

*Texture, upper and lower surfaces.*—Coarse, rough; minute pubescence.

*Venation pattern.*—Pinnate; arcuate.

*Color.*—Developing foliage, upper surface: 146A. Developing foliage, lower surface: 146B. Fully expanded foliage, upper surface: 147A; venation, 146B. Fully expanded foliage, lower surface: 147B; venation, 146D.

*Petiole.*—Length: About 6 mm. Diameter: About 1 mm. Texture, upper and lower surfaces: Pubescent. Color, upper and lower surfaces: 146C.

Flower description:

*Flower arrangement and habit.*—Solitary tubular flowers arranged in hemispherical axially umbels; flowers face mostly upward or outward. Freely flowering habit with potentially two inflorescences developing per node, each umbel with about 28 flowers.

*Natural flowering season.*—Spring until frost in the autumn; flowering continuous during this period.

*Flower longevity on the plant.*—About four to five days. Flowers not persistent.

*Fragrance.*—Faint; fruity.

*Inflorescence height.*—About 1.8 cm.

*Inflorescence diameter.*—About 3.5 cm.

*Flowers.*—Appearance: Flared trumpet, corolla fused, four-parted. Diameter: About 9 mm. Depth (height): About 1.5 cm.

*Flower buds.*—Length: About 1.3 cm. Diameter: About 4 mm. Shape: Elongate, oblong. Color: 10A.

*Corolla.*—Arrangement: Single whorl of four fused petals. Petal lobe length: About 4 mm. Petal lobe width: About 3 mm to 5 mm. Petal lobe shape: Roughly ovoid. Petal lobe apex: Rounded or mucronate. Petal margin: Entire, slightly sinuate. Petal texture, upper surface: Smooth, glabrous. Petal texture, lower surface: Pubescent. Color: When opening, upper surface: 10A. When opening, lower surface: 10C. Fully opened, upper surface: 13B; color towards the apex becoming closer to 12C with development; throat, 17A. Fully opened, lower surface: 13C; tube, 15C.

*Calyx.*—Appearance: Short and narrow tubular calyx. Length: About 3 mm. Diameter: About 1.5 mm. Sepal apex: Acute. Sepal margin: Entire. Sepal texture, upper surface: Smooth, glabrous. Sepal texture, lower surface: Pubescent. Sepal color, upper surface: 145C. Sepal color, lower surface: 145A.

*Peduncles.*—Length: About 4.7 cm. Diameter: About 1 mm. Strength: Strong. Texture: Pubescent. Color: 146B.

*Pedicels.*—Length: Less than 1 mm. Diameter: Less than 1 mm. Color: Close to 146B.

*Reproductive organs.*—Stamens: Quantity/arrangement: Four per flower, adanate to floral tube. Filament length: About 2 mm. Filament color: 13B. Anther shape: Oval. Anther length: Less than 1 mm. Anther color: 13B. Pollen amount: Scarce. Pollen color: 13B. Pistils: Quantity: One per flower. Pistil length: About 4 mm. Stigma shape: Rounded. Stigma color: 145A. Style length: About 2.5 mm. Style color: 145C. Ovary color: 145A. Fruits/seed: Fruit and seed development have not been observed.

Temperature tolerance: Plants of the new *Lantana* have been observed to tolerate temperatures from about 4° C. to about 38° C.

Pathogen/pest resistance: Plants of the new *Lantana* have not been observed to be resistant to pests and pathogens common to *Lantanas*.

It is claimed:

1. A new and distinct *Lantana* plant named 'Robpwcrm' as illustrated and described.

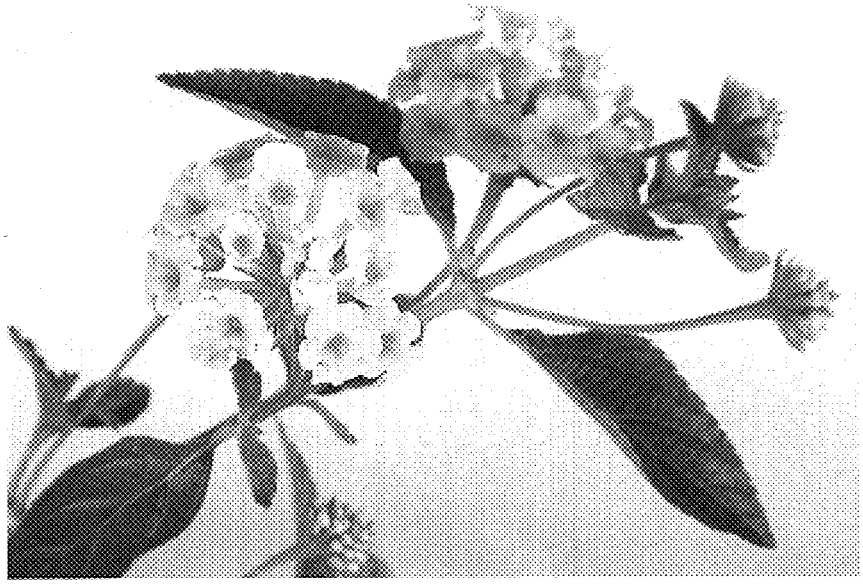
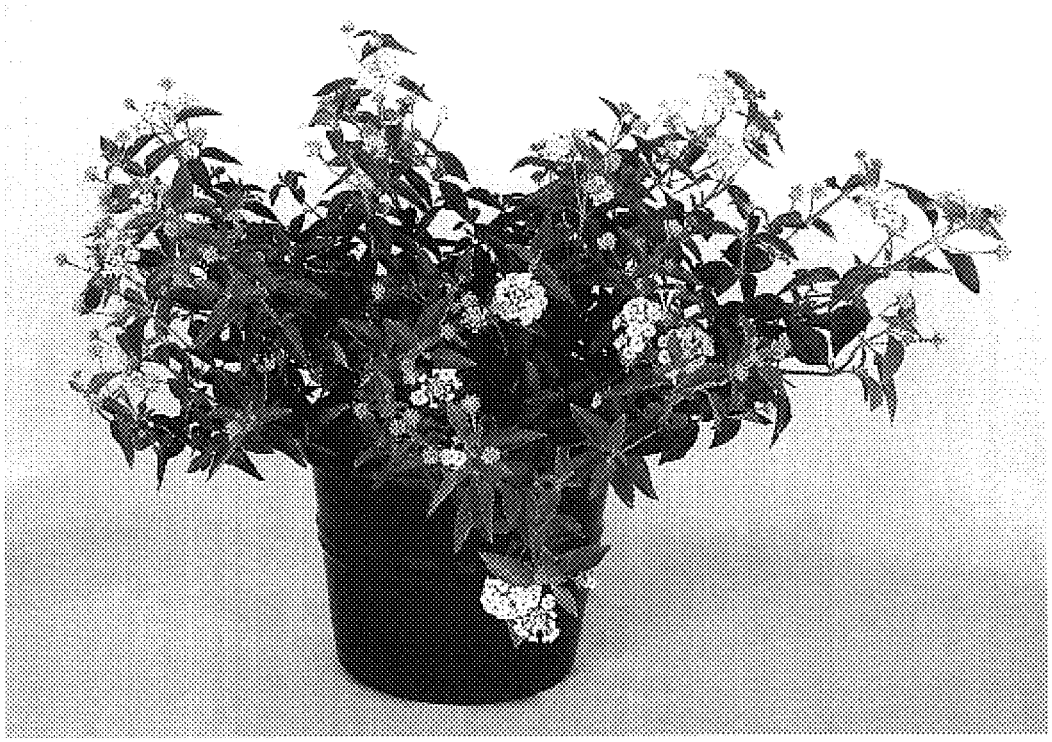

* * * * *